United States Patent [19]

Lentfer

[11] Patent Number: 4,654,299
[45] Date of Patent: Mar. 31, 1987

[54] PROCEDURE FOR THE IRREVERSIBLE BINDING OF PROTEINS ONTO POLYSTYRENE SURFACES WITH RETENTION OF THEIR BIOLOGICAL ACTIVITY, POLYSTYRENE SURFACES OBTAINED BY THIS PROCEDURE, AND THEIR USE

[75] Inventor: Dierck Lentfer, Rodgau, Fed. Rep. of Germany

[73] Assignee: Mallinckrodt Diagnostica (Germany) GmbH, Dietzenbach-Steinberg, Fed. Rep. of Germany

[21] Appl. No.: 592,046

[22] Filed: Mar. 21, 1984

[30] Foreign Application Priority Data

Mar. 31, 1983 [DE] Fed. Rep. of Germany ....... 3311889

[51] Int. Cl.⁴ .................. G01N 33/53; G01N 33/545; G01N 33/549
[52] U.S. Cl. ........................ 435/7; 436/531; 436/532; 436/800; 436/804; 436/810
[58] Field of Search ............... 436/531–532, 436/810, 800, 804; 435/7

[56] References Cited

U.S. PATENT DOCUMENTS

| | | | |
|---|---|---|---|
| 3,846,306 | 11/1974 | Barker et al. | 436/531 |
| 4,017,597 | 4/1977 | Reynolds | 436/531 |
| 4,217,338 | 8/1980 | Quash | 436/531 |
| 4,225,784 | 9/1980 | Barett | 436/531 |
| 4,253,844 | 3/1981 | Limet et al. | 436/532 |
| 4,267,234 | 5/1981 | Rembaum | 436/531 |
| 4,278,651 | 7/1981 | Hales | 436/531 |
| 4,342,739 | 8/1982 | Kakimi et al. | 436/531 |
| 4,357,311 | 11/1982 | Schutt | 436/532 |
| 4,506,019 | 3/1985 | Leg | 436/531 |

Primary Examiner—Christine M. Nucker
Attorney, Agent, or Firm—R. J. Klostermann; L. N. Goodwin; R. G. Jackson

[57] ABSTRACT

A procedure for the immobilization of proteins on polystyrene surfaces which includes a pre-treatment of the polystyrene surface with a bis-diazonium compound of the general formula I where

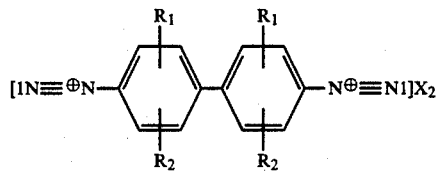

R1 stands for a hydrogen atom, a halogen atom, an alkyl group, an alkoxy group or a nitro group and where
R2 stands for a hydrogen atom, a halogen atom or an alkyl group and where X stands for an anion and the subsequent adsorption of the protein on the surface pretreated.

Proteins immobilized by its procedure may be used in immunoassays.

10 Claims, No Drawings

PROCEDURE FOR THE IRREVERSIBLE BINDING OF PROTEINS ONTO POLYSTYRENE SURFACES WITH RETENTION OF THEIR BIOLOGICAL ACTIVITY, POLYSTYRENE SURFACES OBTAINED BY THIS PROCEDURE, AND THEIR USE

The invention concerns a procedure for the irreversible binding of proteins onto polystyrene surfaces, polystyrene surfaces obtained by this procedure and their use.

The immobilization of biological active proteins, such as enzymes, antibodies, antigens, finds broad application for different purposes, e.g. in enzyme reactors, for affinity chromatography, for immune adsorption, for ligand assays with solid-phase separation.

A special application is that of immobilized antigens and antibodies in the field of immunoassays (e.g. RIA, ELISA, etc.) for the phase separation in heterogeneous systems. The heterogeneous immunoassay systems include one or more steps, by whch a separation between bound and unbound portions of an analyte or reagent is achieved. The binding consists in antigen-antibody interactions.

The necessary separation can be performed elegantly, if the given binding partner (the specific antibody or the specific antigen) is irreversibly immobilized in reactive form on a smooth macroscopic surface. The immobilization may be performed for example, on the inner wall of the reaction vessel or on a bead which is covered by the reaction liquid.

A smooth macroscopic surface is preferred to avoid a mechanical separation by for example, centifugation or filtration as necessary by microscopically distributed surfaces (e.g. latex) and to decrease the amount of adhering reaction liquid (which is high with porous materials as for example gels).

Polystyrene surfaces coated adsorptively with proteins have found broad application in solid-phase separation immunoassay systems. Polystyrene offers the following advantages:
  low price
  clear, transparent
  reaction vessels of various kinds and beads commercially available.

The main advantage of adsorptive coating is its simplicity: a protein solution of appropriate concentration is brought into contact with the plastic surface under protein adsorbing conditions for a certain time, for example, 3-16 hours, thereafter the protein solution is removed and the surface is washed. The yield is up to 60% of protein immobilized, the density is in the orger of 1 ug of protein per cm². The advantage of simple coating is contrasted by drawbacks in the use: with weaker binding proteins a sufficient density of coating is only achieved with a considerable excess of protein; immobilization is reversible, under assay conditions (i.e. in presence of other proteins or of Tween 20 for the prevention of unwanted subsequent adsorption) or a loss of protein immobilized (bleeding out) is observed, which may interfere with the assay.

Attempts exist to overcome these disadvantages of the adsorptive immobilization by introduction of a covalent binding to the plastic surface. Various procedures have been described, which make use of glutarialdehyde as a coupling reagent. The mechanism involved has not been identified, especially whether the improvements observed are due to an involvement of the glutardialdehyde in the connection to the plastic material, or if they are caused by a stabilization of the biologically active conformation of the protein by intramolecular bridging.

In addition, y-irradiation (cobalt-sterilization) of polystyrene articles is used for the improvement of the adsorptive binding of proteins, but this increases considerably the prices of commercially available articles.

The objective of the present invention is therefore to make available a simple and low-price procedure for the irreversible binding of proteins onto polystyrene surfaces with retention of their biological activity.

This objective is achieved:

(a) by the pre-treatment of the polystryene surface with a bis-diazonium compound of the general formula I

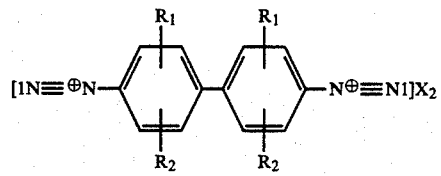

where
  R1 stands for a hydrogen atom, a halogen atom, an alkyl group, an alkoxy group or a nitro group and where
  R2 stands for a hydrogen atom, a halogen atom, an alkyl group and where X stands for a halogen ion or a tetrafluoroborate-ion and (b) by the subsequent, adsorption of the protein to the surface treated in this way.

Alkyl or alkoxy groups are those with 1 to 4 carbon atoms, preferably methyl and methoxy. Halogen atoms are bromine, chlorine and fluorine, preferably chlorine. Preferred bis-diazonium compounds are those of the general formula I a

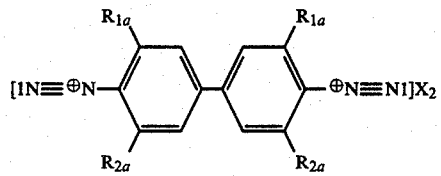

where
  R1a stands for a hydrogen atom, a methyl group, or a methoxy group and where
  R2a stands for a hydrogen atom or a methyl group and where
  X stands for a halogen ion or tetrafluoroborate-ion.

A preferred compound of formula Ia is that, where R1a stands for a methoxy group, R2a stands for a hydrogen atom and X for $Cl^-$ or $BF_4^-$.

Alternatively the bis-diazonium compounds I or Ia may be used in other forms commercially available, e.g. as complexes. The polystyrene surfaces may exist in any given form; e.g. as reaction vessels, as reagent tubes, beakers, cuvettes, columns, microtiter or microtest plates, or as parts, e.g. beads, rods, discs or plates. Such polystyrene surfaces are well known to those skilled in the art and are readily available.

The pre-treatment (activation) is performed under pre-treatment conditions, e.g., at temperatures from about −5° to about +30° C., preferably 4°–10° C. and activation time is from about 5 to 60 min. The concentration of the bis-diazonium compound is typically between about $10^{-5}$ and $10^{-1}$ moles per liter, preferably in a buffer of pH 6–8. Suitable salts like NaCl, KI or NaIO$_4$ may be added for stabilization in stabilizing amounts.

Before the subsequent adsorption of protein, the polystyrene surfaces are cleaned from unreacted bis-diazonium compound I by washing with buffer and/or water. The adsorption may be performed immediately after activation or with a time lag.

The subsequent adsorption of the protein is performed under protein adsorbing conditions by incubation of the protein, dissolved e.g. at a concentration from about $10^{-9}$ to $10^{-3}$ g/ml, preferably $10^{-6}$ to $10^{-4}$ g/ml in a buffer of pH 6–8, for about 1 to about 72 hours. Any protein may be used, e.g. antibodies, antigens, hapten protein conjugates, antibody-binding proteins, for example, staphylococcal protein A or complement component $C_{1q}$, enzymes, lectins.

The polystyrene surface with the absorbed (immobilized) protein may be used for the desired purposes immediately after the adsorption or after storage.

The activation of the polystyrene surfaces leads to a practically irreversible binding of proteins, which enables an increase in sensitivity, and decrease in material consumption in e.g. immuno assays (no bleeding out). The activation leads to a stabilization of the adsorbed proteins, especially when a subsequent drying step is performed.

The polystyrene articles may be distributed commercially after the activation or after the protein adsorption or in the form of a kit. If distributed in the form of a kit, this includes besides the polystyrene article a test tube or a microtest plate, other usual components, for example, a labelled antibody and a detecting reagent for the marker, e.g. a chromogenic substrate.

The bis-diazonium compounds I are well known and are prepared from the corresponding benzidines according to well-known procedures. (Houben-Weyl, Methoden der organischen Chemie, Georg Thieme Verlag Stuttgart, Vol. 10/3, pp. 1–212, esp. 46; Ullmanns Enzyklopädie der technischen Chemie, 4. Auflage Verlag Chemie Weinheim, Vol. 8, p. 356 ff.)

The following examples serve for the illustration of the invention, without restricting it. Temperatures are given in °C.

GENERAL WORKING PROCEDURE

1. The polystyrene surfaces are completely covered for 30 minutes at 40° with a solution of 0.001 moles per liter of FBS(BF$_4$)$_2$ (FBS—Fast Blue B Salt=bis-diazotized o-dianisidine) in 0.01 moles per liter sodium phosphate buffer pH 6.8, under protection from direct light. The FBS solution is removed, the polystyrene articles are washed 3 times with 0.01 mole per liter sodium phosphate buffer.

2. Protein Adsorption

The polystyrene articles pre-treated according to 1. are incubated with a solution or suspension of the desired protein (maximal 2 ug of protein per cm$^2$ of surface to be coated) in 0.01 moles per liter sodium phosphate buffer pH 6.8 for 16 hours at 4°. The protein solution is removed, weakly bound protein is removed by incubation with sodium phosphate buffer containing 0.1% Tween ®20 (Polysorbate 20=Polyoxyethylene 20 sorbitan monolaurate) for 1 hour.

SPECIFIC EXAMPLES

1. $^{125}$I-labled, y-globulin (from goat, 140000 cpm/ug protein) was coated according to A.2. onto untreated polystyrene tubes (11×65, Greiner, Germany) and onto the same tubes pre-treated according to A.1. The volumes of the FBS and y-globulin solutions were 1 ml each, the y-globulin solution was applied in a range of graduated concentrations: 1; 0.5; 0.25; 0.125; and 0.0625 and 0.03125 ug/ml.

Table 1 shows the results obtained:

TABLE 1

| $^{125}$I-Y-globulin applied (ug) | Coating yield (in %) | | | |
|---|---|---|---|---|
| | without FBS pre-treatment | | with FBS pre-treatment | |
| | I | II | I | II |
| 1 | 64.8 | 24.9 | 57.2 | 54.4 |
| 0.5 | 69.1 | 20.3 | 62.6 | 59.6 |
| 0.25 | 66.2 | 18.5 | 60.6 | 57.1 |
| 0.125 | 68.8 | 18.7 | 62.8 | 60.5 |
| 0.0625 | 65.7 | 17.3 | 62.4 | 59.2 |
| 0103125 | 59.5 | 14.9 | 67.6 | 63.3 |

I: before treatment with Tween
II: after treatment with Tween

The coating yield without FBS-pre-treatment was about 65%, with FBS pre-treatment it was about 60%. If both kinds of coated tube were incubated for 1 hour with a 0.1% solution of Tween 20 in physiological saline, the coating yield of the tubes without FBS pre-treatment dropped to about 20%, whereas it remained practically unchanged with the pre-treated tubes.

2. According to B.1. untreated and FBS pre-treated polystyrene tubes were ocated with Theophylline-antiserum (from rabbit, 1 ml per tube, dilution 1:36000). The tubes were subsequently washed for 1 hour with a 1% solution of polyvinyl alcohol (low molecular weight type) in 0.01 mole per liter potassium phosphate buffer pH 7.4 The coated tubes were incubated for 1 hour at room temperature with 1 ml each of a solution of Theophylline-peroxidase conjugate ($10^{-7}$ g/ml, about 2 molecules of Theophylline per molecule of horse radish peroxidase) in 0.01 moles per liter potassium phosphate buffer pH 7.4 containing 0.1% gelatine, 0.9% NaCl and 0.03% magnesium-1-anilinonaphthalene-8-sulfonate. Subsequently the tubes were washed with cold tap water (3 times). The determination of antibody-bound enzyme activity was achieved by incubating the tubes for 20 minutes at room temperature with 1 ml of a solution containing 0.33 mg/ml o-phenylenediamine and 0.05 mg/ml H$_2$O$_2$ in 0.1 mol per liter tris-acetate buffer pH 5.6. The reaction was stopped by addition of 1 ml of 1 mole per liter sulfuric acid. The optical density at 492 was determined photometrically. The result was 0.129 for untreated and 0.944 for FBS pre-treated tubes.

3(a) According to B.1. untreated and FBS pre-treated polystyrene microtiter plates were coated with 0.1 ml/cup of various dilution sof a streptolysin-o-preparation (0.131 mg/ml protein; about 4000 IU/mg protein).

1:2 dilution series (volume 0.1 ml/cup) of an anti-streptolysin standard serum (Behring-Werke, Marburg; 10 IU/ml) were prepared in the differently coated microtiter plates, using 0.1 mole per liter Tris-HCl buffer pH 7.8 with 0.1% Tween 20 as the diluent. The plates were incubated for 30 minutes at 37° C., the serum dilutions were removed and the plates were washed once with cold tap water. To each cup 0.1 ml of a solution containing 2 ug/ml of an anti-Hu IgG-peroxidase conjugate (rabbit IgG against human IgG, coupled to horse radish peroxidase) was added and incubated for 30 minutes at 37° C. After removal of the conjugate solution the plates were washed 3 times with cold tap water. For the detection of peroxidase activity immobilized by immuno adsorption, 0.1 ml per cup of a substrate mixture (0.16 mg/ml o-tolidine, 0.05 mg/ml $H_2O_2$ in 0.1 mole per liter tris-citrate buffer pH 5) was added and incubated for 30 minutes at room temperature. For evaluation the highest serum dilution still producing a blue color was identified.

The results are shown in Table 2.

TABLE 2

| Streptolysin dilution used for coating | Highest positive dilution of standard serum | |
|---|---|---|
| | without FBS | with FBS |
| 1:20 | 40 | 80 |
| 1:40 | 20 | 80 |
| 1:80 | 10 | 20 |

3(b) The differences are even more pronounced, if the coating procedure is followed by a drying step (3 hours at room temperature in vacuo at 0.1 mbar), which is advantageous for longer storage.

Table 3 shows the results obtained according to 3(a) (Streptolysine dilution 1:80; highest positive dilutions given for standard serum and the patient sera). The better performance of the activated plates can be seen.

TABLE 3

| | Highest Positive Dilution of Serum Sample | |
|---|---|---|
| | without FBS | with FBS |
| Standard serum | negative | 60 |
| Patient I | 200 | 6400 |
| Patient II | 150 | 6400 |
| Patient III | 50 | 4800 |

4. According to B.1. untreated or FBS-treated polystyrene microtiter plates were coated with 0.1 ml per cup of a solution containing 0.01 mg/ml of a glycoprotein fraction from *Candida albicans* (preprepared by Dr. H. Mauch, University des Saarlandes, Homburg/Saar, Germany).

1:4600 dilutions of the serum samples given below in 0.1 mole per liter Tris-HCl buffer pH 7.8 with 0.1% Tween ® 20 were prepared and were incubated for 1 hour at room temperature with 0.1 ml per cup in the coated plates.

Serum A: healthy proband with low antibody concentration against *Candida albicans*.

Serum B: pooled sera from healthy donors.

Serum C: patients serum I with elevated antibody concentration against *Candida albicans*.

serum D: patients serum II with elevated antibody concentration against *Candida albicans*.

After removal of the serum samples the plates were washed once with cold tap water. To each cup 0.1 ml of a solution containing 0.1 ug/ml of an anti-Hu IgG-peroxidase conjugate (rabbit IgG against human IgG coupled to horse radish peroxidase) was added and incubated for 1 hour at room temperature. After removal of the conjugate solution the plates were washed 3 times with cold tap water. For the detection of peroxidase activity immobilized by immunoadsorption 0.1 ml per cup of a substrate mixture (0.1 mg/ml 3,3',5,5'-Tetra methylbenzidine, 0.06 mg/ml $H_2O_2$ in 0.1 mole per liter tris-citrate buffer pH 5) was added and incubated for 30 minutes at room temperature. The reaction was stopped by addition of 0.1 ml per cup of 1 mole per liter sulfuric acid and the adsorption at 455 nm was determined photometrically in a Kontron SLT 210 micro-titer plate reader.

The results are shown in table 4.

TABLE 4

| | Absorption at 455 nm | |
|---|---|---|
| Serum Sample | without FBS | with FBS |
| A | 0.078 | 0.177 |
| B | 0.154 | 0.566 |
| C | 0.308 | 1.088 |
| D | 0.529 | 1.662 |

5. Kit for the determination of antibodies against streptolysine-o in human serum.

The kit consists of:

(a) a micro-titer plate coated with Streptolysine-o according to the invention described, serving as an antigen-coated reaction vessel (b) a solution of conjugate of rabbit IgG and horse radish peroxidase, directed against human IgG (lyophilized, if necessary)

(c) 0.1 mole per liter tris citrate buffer pH 5 for the peroxidase reaction (d) a stock solution of 3,3',5,5'-tetramethylbenzidine in dimethylsulfoxide (0.1 mg/ml), serving as a chromogen for the peroxidase reaction (e) a solution of hydrogen peroxide (3%) for the peroxidase reaction (f) a 0.1 mole per liter tris-HCl buffer solution pH 7.8, containing 0.1% Tween ® 20, serving as a diluent for serum samples and antibody-peroxidase conjugate.

What is claimed is:

1. Procedure for the irreversible binding of proteins onto a polystyrene surface, comprising (a) treating a polystyrene surface with a bis-diazonium compound under bis-diazonium compound treating conditions of the general formula I,

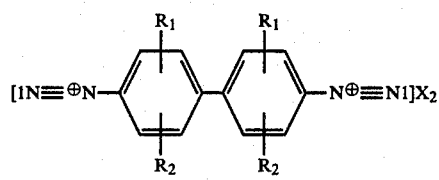

where

R1 stands for a hydrogen atom, a halogen atom, an alkyl group, an alkoxy group or a nitro group and where R2 stands for a hydrogen atom, a halogen atom, an alkyl group and where X stands for an anion and (b) by thereafter adsorbing a protein on to the surface under protein adsorbing conditions.

2. Procedure according to claim 1, where each R1 is ortho to the nitrogen group and stands for a hydrogen atom, a methyl group or a methoxy group and where each R2 is ortho to the nitrogen group and stands for a hydrogen atom, a methyl group, and where X stands for a halogen or tetrafluoroborate ion.

3. Procedure according to claim 2, where R1 a stands for a methoxy group, R2 a stands for a hydrogen atom and X stands for $Cl^-$ or $BF_4^-$.

4. Procedure according to claim 1, where the bis-diazonium compound is in the form of a complex.

5. Procedure according to claim 1, wherein the protein is an antibody, an antigen, a hapten protein conjugate, an antibody-binding protein, an enzyme or lectin.

6. A bis-diazonium treated polystyrene vessel or bead suitable for adsorbing proteins prepared by step (a) of claim 1.

7. A bis-diazonium treated polystyrene vessel or bead having proteins adsorbed thereto prepared according to the procedure of claim 1.

8. Polystyrene articles according to claim 7, wherein the protein is an antibody, antigen, hapten protein conjugate, antibody-binding protein, enzyme or lectin.

9. In an immunochemical or enzymatical method for determining the concentration of an analyte in a measured amount of an aqueous sample wherein said aqueous solution is contacted with:

(1) an insoluble carrier to which has been attached a biologically active substance capable of reacting with said analyte and (2) a measured amount of a tracer labeled member to form after substantial equilibration a two-phase system containing a solid phase having a portion of the labeled member and unlabeled member bound to said biologically active substance and a liquid phase containing the balance of the unbound labeled member and unlabeled member, (3) the two phases separated and the concentration determined, (4) the improvement comprising using as the insoluble carrier the article prepared by the procedure of claim 1.

10. A method according to claim 9 wherein the tracer label is selected from the group consisting of a radio label, an enzyme label, a fluorescent label, and a luminescent label.

* * * * *